(12) United States Patent
Carron et al.

(10) Patent No.: US 9,097,675 B2
(45) Date of Patent: **\*Aug. 4, 2015**

(54) LYOPHILIZATION OF COLLOIDAL METALS FOR SURFACE ENHANCED RAMAN SCATTERING

(75) Inventors: Keith T. Carron, Centennial, WY (US);
Bryan Hubert Ray, Laramie, WY (US);
Roberta A. Sulk, Laramie, WY (US)

(73) Assignee: University of Wyoming, Laramie, WY (US)

( \* ) Notice: Subject to any disclaimer, the term of this patent is extended or adjusted under 35 U.S.C. 154(b) by 0 days.

This patent is subject to a terminal disclaimer.

(21) Appl. No.: 13/160,985

(22) Filed: Jun. 15, 2011

(65) Prior Publication Data

US 2011/0294230 A1 Dec. 1, 2011

Related U.S. Application Data

(62) Division of application No. 10/177,194, filed on Jun. 21, 2002, now abandoned.

(60) Provisional application No. 60/300,270, filed on Jun. 21, 2001.

(51) Int. Cl.
*G01N 33/553* (2006.01)
*G01N 21/65* (2006.01)
*G01N 33/543* (2006.01)

(52) U.S. Cl.
CPC ........ *G01N 21/658* (2013.01); *G01N 33/54373* (2013.01); *G01N 33/54393* (2013.01); *Y10T 436/25* (2015.01)

(58) Field of Classification Search
CPC .......... G01N 21/658; G01N 33/54373; G01N 33/54393; Y10T 436/25

USPC ......................................................... 436/526
See application file for complete search history.

(56) References Cited

U.S. PATENT DOCUMENTS

| | | | |
|---|---|---|---|
| 3,799,742 A * | 3/1974 | Coleman | 422/417 |
| 4,043,678 A * | 8/1977 | Farrell et al. | 356/246 |
| 4,450,231 A * | 5/1984 | Ozkan | 435/7.92 |
| 4,920,061 A | 4/1990 | Poynton et al. | |

(Continued)

FOREIGN PATENT DOCUMENTS

WO 9859234 12/1998

OTHER PUBLICATIONS

L. Rivas et al, "Growth of Silver Collodial Particles Obtained by Citrate Reduction to Increase the Raman Enhancement Factor," Instituto de Estructura de la Materia, CSIC, Serrano 121, E-28006 Madrid, Spain and Departamento de Quimica Organica y Biologia, Universidad Nacional de Educacion a Distancia, Senda del Rey s/n E-28040 Madrid Spain, pp. 574-577, Langmuir 2001.

(Continued)

*Primary Examiner* — Bao Thuy L Nguyen
*Assistant Examiner* — Pensee Do
(74) *Attorney, Agent, or Firm* — Kaplan Breyer Schwarz & Ottesen, LLP

(57) ABSTRACT

An assay and method of making same for use in SERS spectroscopy. The assay includes colloidal particles of a metal, which have been lyophilized. The lyophilized particles of metal produce a SERS active solution when reconstituted. The lyophilized particles of metal may be provided in a container in an assay system.

14 Claims, 8 Drawing Sheets

(56) References Cited

U.S. PATENT DOCUMENTS

| | | | |
|---|---|---|---|
| 5,102,788 A * | 4/1992 | Cole | 435/7.9 |
| 5,169,789 A | 12/1992 | Bernstein | |
| 5,252,459 A | 10/1993 | Tarcha et al. | |
| 5,255,067 A | 10/1993 | Carrabba et al. | |
| 5,376,556 A * | 12/1994 | Tarcha et al. | 436/525 |
| 5,637,508 A * | 6/1997 | Kidwell et al. | 436/525 |
| 5,705,207 A | 1/1998 | Cook et al. | |
| 5,759,774 A | 6/1998 | Hackett et al. | |
| 5,869,346 A * | 2/1999 | Xiaoming et al. | 436/525 |
| 6,391,652 B2 | 5/2002 | Okada et al. | |
| 6,770,488 B1 | 8/2004 | Carron et al. | |
| 7,776,610 B2 | 8/2010 | Carron et al. | |
| 7,993,933 B2 | 8/2011 | Carron et al. | |
| 2003/0231304 A1 | 12/2003 | Chan et al. | |
| 2004/0135997 A1 | 7/2004 | Chan et al. | |

OTHER PUBLICATIONS

1982 American Chemical Society—J. Phys. Chem 1982, 86, 3391-3395—"Adsorption and Surface-Enhanced Raman of Dyes on Silver and Gold Sols," by P.C. Lee and D. Meisel.

Roberta Sulk, Collin Chan, Jason Guicheteau, Cieline Gomez, J.B.B. Heyns, Robert Corcoran and Keith Carron, "Surface Enhanced Raman Assays (SERA): Measurement of Bilirubin and Salicylate," J. Raman Spectrose, 1999, 30, 853-859.

Non-Final Office Action dated Jul. 5, 2005 issued in co-pending U.S. Appl. No. 10/177,194, filed Jun. 21, 2002 of Keith T. Carron.

Non-Final Office Action dated Dec. 29, 2005 issued in co-pending U.S. Appl. No. 10/177,194, filed Jun. 21, 2002 of Keith T. Carron.

Final Office Action dated Jun. 14, 2006 issued in co-pending U.S. Appl. No. 10/177,194, filed Jun. 21, 2002 of Keith T. Carron.

Non-Final Office Action dated Feb. 23, 2007 issued in co-pending U.S. Appl. No. 10/177,194, filed Jun. 21, 2002 of Keith T. Carron.

Final Office Action dated Nov. 1, 2007 issued in co-pending U.S. Appl. No. 10/177,194, filed Jun. 21, 2002 of Keith T. Carron.

Non-Final Office Action dated Jul. 28, 2008 issued in co-pending U.S. Appl. No. 10/177,194, filed Jun. 21, 2002 of Keith T. Carron.

Final Office Action dated Jul. 24, 2009 issued in co-pending U.S. Appl. No. 10/177,194, filed Jun. 21, 2002 of Keith T. Carron.

Non-Final Office Action dated Dec. 20, 2010 issued in co-pending U.S. Appl. No. 10/177,194, filed Jun. 21, 2002 of Keith T. Carron.

* cited by examiner

LYOPHILIZATION OF COLLOIDAL METALS FOR SURFACE ENHANCED RAMAN SCATTERING

This application is a divisional application of U.S. application Ser. No. 10/177,194, filed Jun. 21, 2002 which application claims the benefit of U.S. Provisional Application No. 60/300,270, filed Jun. 21, 2001.

FIELD OF THE INVENTION

This invention relates to Raman spectroscopy and Surface Enhanced Raman Scattering (SERS). More specifically, this invention relates to a stable form of colloidal metal particles that when reconstituted, produces a SERS active solution.

BACKGROUND OF INVENTION

Raman spectroscopy stems from the inelastic scattering of light by molecular vibrational energy levels. Raman spectroscopy as an analytical tool has been known for decades, and is particularly popular for several reasons. For example, molecular composition can be determined in the presence of water. Visible light can be employed for analysis allowing for the use of conventional fiber optics. Unique spectral fingerprints allow for identification and quantification of a wide variety of solids, liquids, and gases. One of the significant disadvantages of Raman spectroscopy is the inadequate sensitivity for trace or ultratrace analysis. This stems from the inherently weak nature of Raman scattering.

In the early 1970s several researchers found an anomalous enhancement of Raman scattering at the surface of certain metals. It has subsequently been found that the metals that have both practicality and strong enhancing properties are silver, gold, and copper. The enhancement is believed to generally come from an electromagnetic effect and in some cases, an enhancement due to the nature of the chemical bond to the metal surface has also been found. The reported enhancement for SERS depends on the structure of the surface and ranges from about $10^5$ to $10^8$. This discovery immediately made it possible to detect very small amounts of material adsorbed to these surfaces. The SERS effect is limited to molecules attached to or in very close proximity with the surface.

The drawback to conventional SERS is that it is limited to analytes that will naturally adsorb to a SERS active metal surface. Thus, while in special cases SERS provides sensitive detection, in most cases it suffers from the inability of the molecule to adsorb to the surface and to benefit from the SERS effect.

A method to overcome the lack of adsorptivity to SERS surfaces by an analyte, is to provide surface coatings that have an affinity for the analyte. An example is an early publication which describes using a surface bound coating in the detection of hydrogen ions at a surface using SERS (Determination of pH with SERS Fiber Optic Probes. Ken I. Mullen, DaoXin Wang, L. Gayle Hurley, and Keith Carron *Anal. Chem.*, 64, 930, 1992). This publication showed that it was possible to permanently attach a coating to a SERS surface and to have the coating provide the affinity for the analyte.

More recently, it has been demonstrated that an irreversible covalent bonding reagent could be used to achieve even more sensitive detection. Furthermore, it was shown that the surface need not be coated with the surface bound reagent, but rather, the reagent could have two reactive sites. One site is analyte specific and the other is surface binding specific. This produces a high affinity permanent bond to the analyte and a high affinity permanent bond to the surface. An example of a dual binding reagent for trace detection is a reagent that binds bilirubin and which has an argentiphillic sulfide group to bind to silver (Surface Enhanced Raman Assays (SERA): Measurement of Bilirubin and Salicylate, Roberta Sulk, Collin Chan, Jason Guicheteau, Cieline Gomez, J. B. B. Heyns, Robert Corcoran, and Keith Canon, *J. Raman Spectrosc.*, 1999, 30, 853-859).

Accordingly, an assay is needed which is capable of producing a SERS active solution that is sensitive to a specific analyte or group of analytes.

SUMMARY OF THE INVENTION

An assay and method of making same is disclosed herein for use in SERS spectroscopy. The assay comprises lyophilized colloidal particles of a metal, which have been lyophilized. The lyophilized particles of metal produce a SERS active solution when reconstituted.

An assay system and method of making same is further disclosed herein for use in SERS spectroscopy. The assay system comprises a container with lyophilized colloidal particles of a metal disposed in a first section thereof. The lyophilized colloidal particles of a metal contained in the container produce a SERS active solution when reconstituted.

A method of analyzing a material is further disclosed herein. The method comprises the steps of: providing a container; placing colloidal particles of a metal in a first section of the container; lyophilizing the colloidal particles of the metal to produce an assay; simultaneously reconstituting and mixing the assay with the material to be analyzed to produce a SERS active solution; performing SERS spectroscopy on the SERS active solution.

DETAILED DESCRIPTION OF THE INVENTION

Figure 1A:
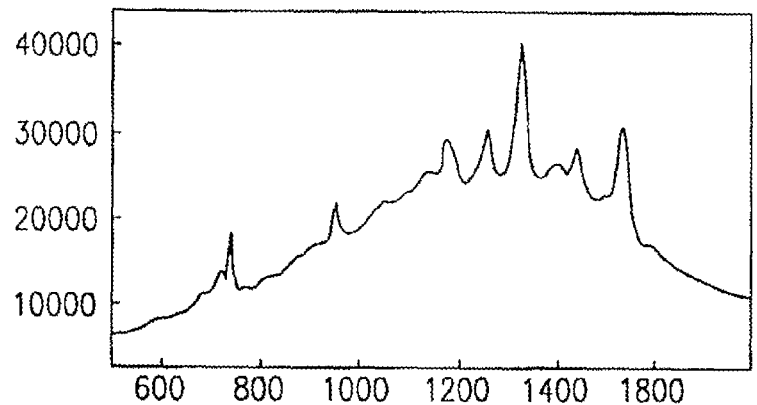
FIG. 1A is a spectrum of reactive blue (RB) 15 dye in fresh colloid suspension.

One aspect of the present invention includes an assay and an assay system for use in Surface Enhanced Raman Scattering (SERS) spectroscopy. Another aspect of the present invention includes methods for preparing the assay and assay system. Still another aspect of the present invention includes a method of analyzing a material using the assay system of the present invention and SERS spectroscopy. Another aspect of the present invention includes a method of analyzing a material using the assay system of the present invention and Surface Enhanced Raman ImmunoAssay (SERIA).

The assay of the present invention comprises a colloidal suspension of noble metal particles, such as silver, gold, or copper particles, which have been lyophilized to dryness using conventional lyophilizing techniques. The lyophilized, colloidal particles of the present invention have long term stability, i.e., the colloidal particles can be stored for a long period of time, and are sensitive to a specific analyte or group of analytes. The lyophilized, colloidal noble metal particles of the present invention produce a SERS active solution, when reconstituted to a colloidal suspension. A specific advantage of having a SERS active solution is that the SERS phenomenon exhibits a signal from material localized near the particle surface. This phenomenon precludes the need for removing excess analyte, impurity, or reagent, that indicates the presence of an analyte, from the sample mixture. This aspect combined with the aspect of a coated particle with long-term stability makes the assay of the invention commercially important.

A particularly important aspect of the assay of the present invention is that the amount of colloidal particles is determined very accurately through a volumetric delivery of a known concentration of colloidal suspension, or delivery of a known mass of colloidal suspension. The mass delivery is enabling to an assay since a large mass of diluted colloid can be used to accurately deliver a small amount of colloid into the chamber of a sample container.

The lyophilized, colloidal particle assay of the present invention may further comprise one or more reagents. The type or types of reagents used will depend upon the particular application or sample to be analyzed. Further, the lyophilized, colloidal particle assay may further comprise one or more antibodies, thereby forming a Surface Enhanced Raman ImmunoAssay (SERIA).

The assay system of the present invention comprises a sample container which contains the lyophilized, colloidal noble metal particles of the present invention. The container typically includes a pretreatment which prevents the lyophilized, colloidal particles from binding to the surface of the chamber of the container, or from binding with each other, thus inhibiting the lyophilized, colloid's ability to be reconstituted to a colloidal suspension. The pretreatment may comprise a wax-like material, such as polyethylene glycol (PEG), or combination of materials, which is applied to the chamber of the container. It should be understood, however, that the pretreatment can be omitted when the sample container is made from a material which possesses the ability to contain the lyophilized, colloid without inhibiting its ability to be reconstituted.

In addition or alternative to pretreating the chamber surface(s) of the container, a material or combination of materials may be added to the colloidal particles, prior to lyophilization, which also immobilizes the lyophilized, colloidal particles within the container and prevents the colloidal particles from binding to the surface of the chamber of the container, or from binding with each other. This pretreatment may also be omitted. This material may also comprise a wax-like material, such as PEG. Another example would be a surfactant material such as sodium dodecylsulfate (SDS). In view of the above, it should be apparent that the assay system of the present invention affords long term stability such that a pretreated assay can be provided for a customer for later use.

Figure 7:
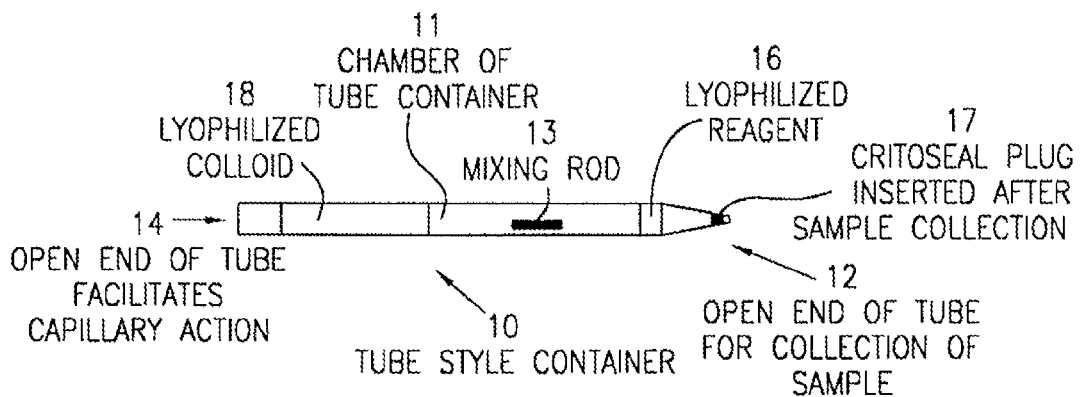
FIG. 7 is a schematic representation of an assay system according to a first illustrative embodiment of the present invention using lyophilized colloids.

In certain applications, one or more reagents must be added in sequential fashion to the assay of the present invention. FIG. 7 shows an assay system according to a first illustrative embodiment of the present invention, which enables sequential addition of such reagents to the assay via physical separation of the reagent and colloid. As shown, a lyophilized assay reagent 16 is located in a chamber 11 of a tube-style container 10 adjacent to a tapered open end 12 thereof, and a lyophilized, colloidal particle assay 18 of the present invention is in the chamber 11 adjacent to an opposing open end 14 of the container 10. This enables one to introduce a sample into the chamber 11 of the container 10 and have it reconstitute and mix with the reagent 16 first by capillary action. Mixing of the sample and reagent is accomplished with a mixing rod 13 disposed in the chamber 11 of the container 10, after which the reagent and sample mixture reconstitutes the lyophilized, colloidal particle assay 18 and mixes therewith. A closure 17, such as a Critoseal, is provided and is inserted in the tapered open end 12 of the container 10 after the sample is collected. It should be understood, that containers of other configurations can be utilized in the assay system of the present invention.

Figure 8:
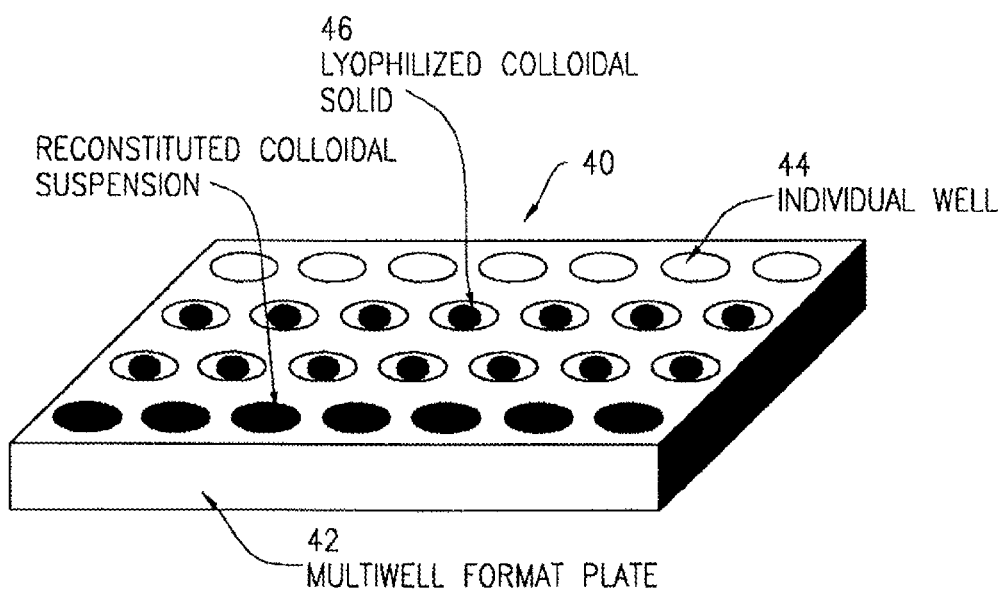
FIG. 8 is a schematic representation of an assay system according to a second illustrative embodiment of the present invention using lyophilized colloids.

Assays are typically performed either individually or multiply. Multiple assays have an advantage that many of the steps involved in the assay can be performed in parallel, thus decreasing the time of the assay. Accordingly, the assay system of the present invention may also comprise a sample container with multiple sample chambers, which enables multiple assays to be performed in parallel, if desired. FIG. 8 shows an system according to a second illustrative embodiment of the invention constructed as a multiformat assay 40 which forms a Surface Enhanced Raman ImmunoAssay (SERIA) where the lyophilized colloid is treated with antibodies and reconstitution is performed in a microwell plate 42 with added sample and reagents. As shown, the microwell plate 42 includes a plurality of wells 44 containing identical lyophilized colloidal particles 46 (colloidal solid) treated with one or more antibodies for analyzing multiple assays at one time. Each lyophilized colloidal solid 46 is reconstituted to a SERS active colloidal solution by the reagent liquids of the assay.

Additionally, as the assay of the present invention takes special advantage of the SERS effect to produce a one-step assay, the sample chamber or chambers include closures, e.g. Critoseal 17 (FIG. 7), which are used for sealing the chambers after introduction of a sample, to prevent contamination of the sample or more importantly, to prevent potential spread of the sample, which may be hazardous to testing personnel or the test facility.

Figure 1B:
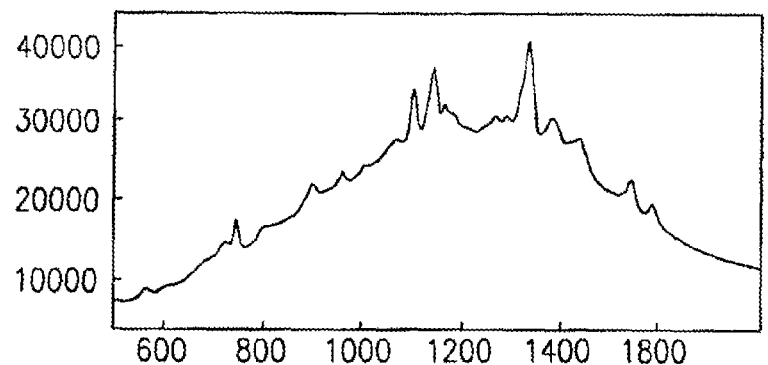
FIG. 1B is a spectrum of a RB 15 dye with reconstituted lyophilized colloidal suspension.

FIGS. 1A and 1B represent the spectral results of an initial study of lyophilized, colloidal noble metal particles. FIG. 1A is a spectrum of reactive blue (RB) 15 dye in fresh colloid suspension having a pH of 6.8. Ten milliliters of this colloid was lyophilized to dryness using conventional lyophilization techniques. The leftover powder was dark gray and very light and susceptible to air currents. The gray powder was then reconstituted with 10 ml of $H_2O$ and 2 µL of an aqueous 1% sodium hydrogen carbonate solution was added to raise the pH from 5.7 to that of the fresh colloid (6.8). Note that no polyethylene glycol (PEG) was added to the reconstituted colloid. The reconstituted colloid was then ultrasonicated for 5 min to produce a cloudy gray solution. The reconstituted colloidal suspension was made to be 60 µm RB 15. FIG. 1B is a spectrum of this reconstituted colloidal suspension with RB 15 dye.

Figure 2A:
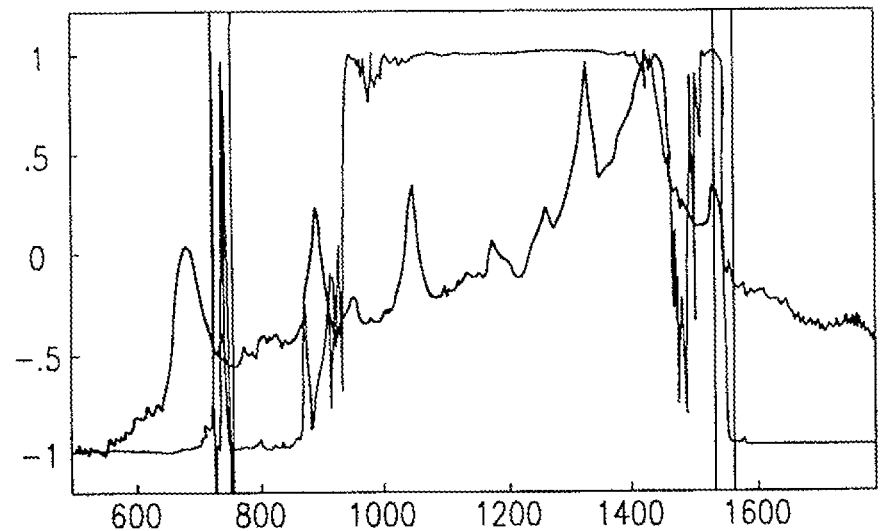
FIG. 2A is a spectrum of a Partial Least Squares (PLS) correlation model using a reconstituted lyophilized colloid and RB 15 dye.
Figure 2B:
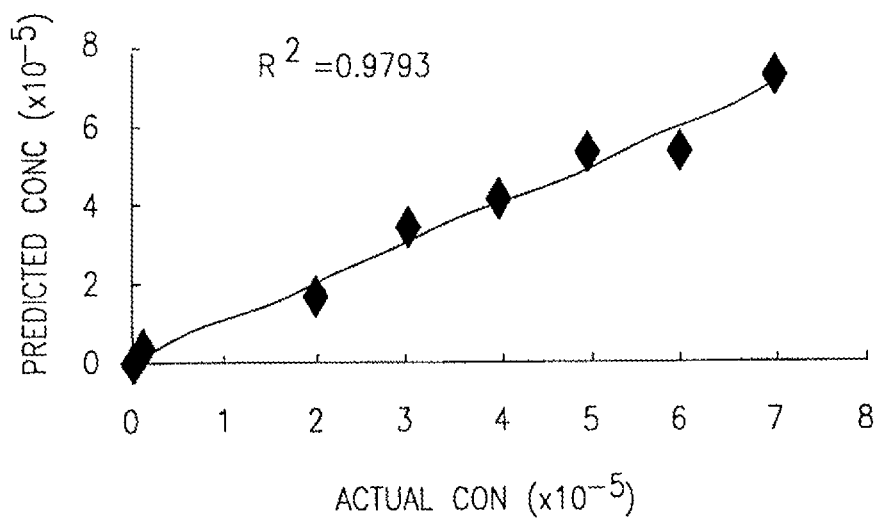
FIG. 2B is a correlation plot between actual concentration and predicted concentration for a reconstituted lyophilized colloid and RB 15 dye solution.

FIG. 2A represents a spectrum of a Partial Least Squares (PLS) correlation model obtained from running a concentration curve of a reconstituted colloid and RB 15 dye. A stock RB 15 solution was prepared by dissolving 0.01283 grams of RB 15 into 10 ml Millipore $H_2O$. Concentrations were prepared from the stock solution ranging from $1.0-6.18 \times 10^{-6}$ M RB 15 using Millipore $H_2O$. The reconstituted colloid (200 µL) was placed into separate 1 ml auto sampler vials. A 20 µL aliquot of each of the RB 15 concentrations was added to separate vials filled with reconstituted colloid. Each mixture was shaken for 20 sec to facilitate an even distribution of RB 15 dye in the colloid. A spectrum of each mixture was taken and recorded, after which PLS was performed on the data set. FIG. 2B shows the result in a correlation plot between actual concentration and predicted concentration with a $R^2=0.9793$. This shows possibilities for lyophilized colloids. However, the lyophilized colloid is a very fine powder that is very susceptible to air currents. Accordingly, in the discussion which follows, polyethylene glycol (PEG) 900 will be introduced into the lyophilizing process to alleviate problems with containing the fine powder and preventing the lyophilized colloidal particles from sticking to the surface of a container.

Figure 3A:
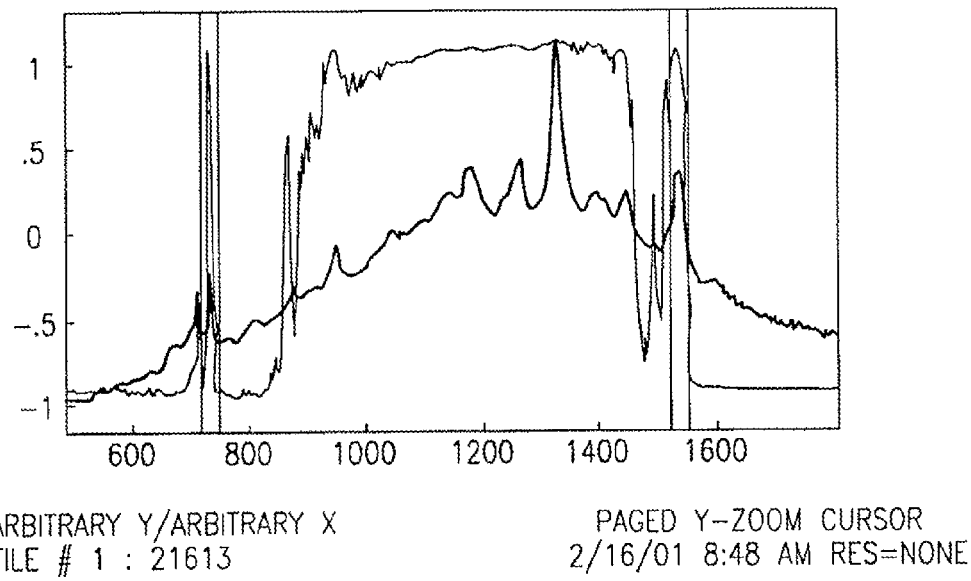
FIG. 3A is a spectrum of a Partial Least Squares (PLS) correlation model using a reconstituted lyophilized colloid with 0.05% w/w polyethylene glycol (PEG) and RB 15 dye.
Figure 3B:
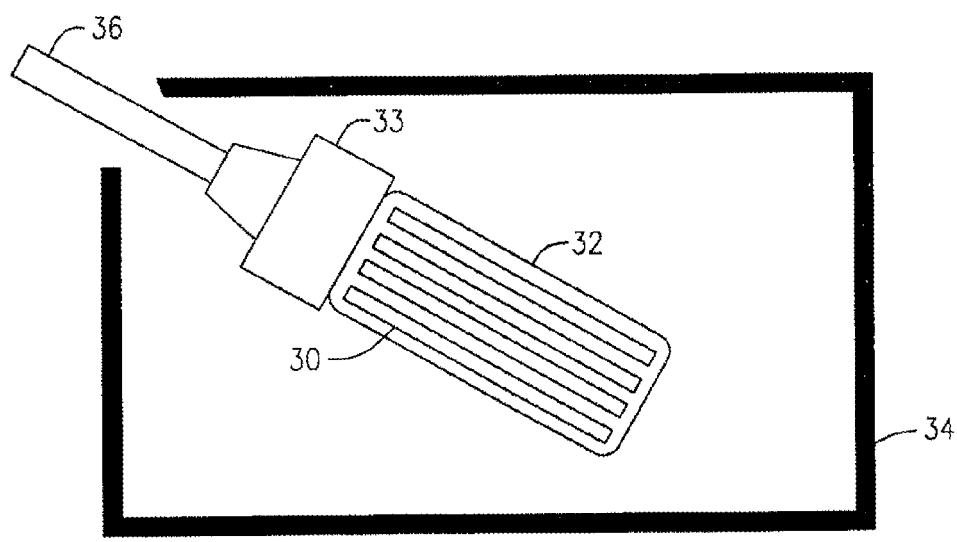
FIG. 3B is a schematic representation of an exemplary apparatus used for producing the lyophilized, colloidal noble metal particles and PEG according to the present invention.
Figure 3C:
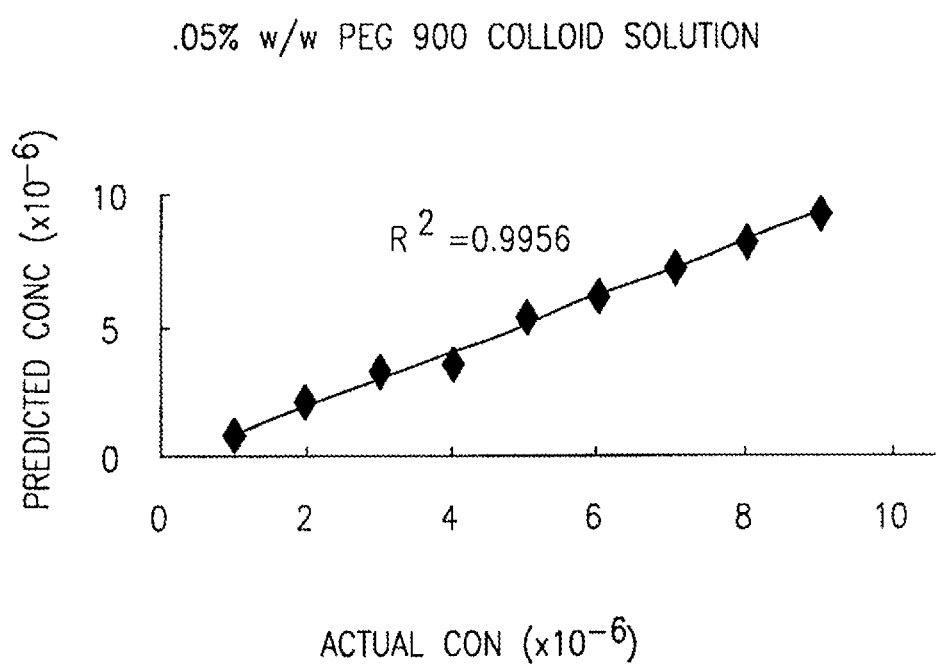
FIG. 3C is a correlation plot between actual concentration and predicted concentration for a reconstituted lyophilized colloid solution with 0.05% w/w PEG and RB 15 dye.

FIG. 3A represents a spectrum of a PLS correlation model using 0.05% w/w PEG 900 m.w./colloid and RB 15 dye. In a 20 mL vial 0.200 g of PEG 900 was diluted to 4.00 g with colloid. A 370 µL Caraway blood collecting tube was submerged into liquid nitrogen until the nitrogen ceases to boil then 100 µL of the solution was injected into the frozen tube. Approximately 40 tubes can be prepared from 4.00 g of PEG 900/colloid solution. As shown in FIG. 3B, the tubes, denoted by numeral 30, were placed in a high vacuum vial 32 with a stopper 33 purchased from Labconco. The vial 32 and stopper 33 was placed in a Styrofoam cooler 34 packed in dry ice and attached to a lyophilizer (not shown), via a steel tube 36 which extends through the stopper, for 24 hours. A stock solution of $10.0 \times 10^{-6}$ M RB 15 was prepared. A range of concentrations from $1.0-10.0 \times 10^{-6}$ M RB 15 was prepared by diluting with Millipore $H_2O$. In separate lyophilized tubes 100 µL of each concentration of RB 15 was injected and a 0.5×5 mm Teflon coated rod was inserted into each tube. A magnet was used to stir the solution with the rod until the lyophilized colloid was completely dissolved, this taking approximately 2 min. The solution was then allowed to flow to the narrow end of the blood collecting tube, a plug of Critoseal was inserted and the tube was placed, plug side down, into the Raman sample holder. A spectrum was taken and recorded for all the different concentrations, after which PLS was performed on the data set. FIG. 3C shows the result in a correlation plot between actual concentration and predicted concentration with a $R^2=0.9956$. When the spectrum of FIG. 2A is compared to the spectrum of FIG. 3A, there are identical peaks and correlation. This indicates that the PEG has little effect on the Raman scattering and it aids in the containment of the lyophilized colloid eliminating susceptibility of the colloid powder to disruption by air currents and/or vibrations in a container. The PLS model from this experiment shows that PEG/colloidal solutions have great potential. Using this model, predictions of 40 samples at the same concentration (100 µL of $4.0 \times 10^{-6}$ RB 15) were made to show reproducibility, i.e., STD=1.99; AVG=4.53; % Corr.=3.6%.

Figure 4A:
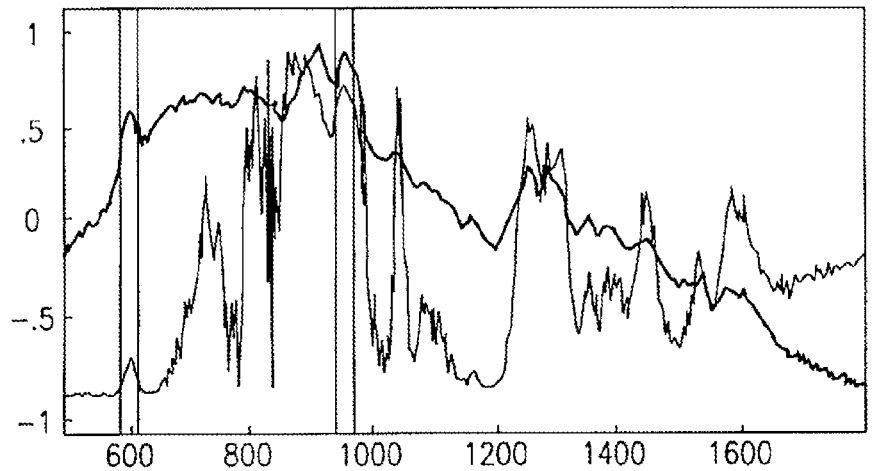
FIG. 4A is a spectrum of a Partial Least Squares (PLS) correlation model using a reconstituted lyophilized colloid with 0.05% PEG, RB 15 dye, and a reagent of Analyte Reactive Coating soluble in Water (ARCW).
Figure 4B:
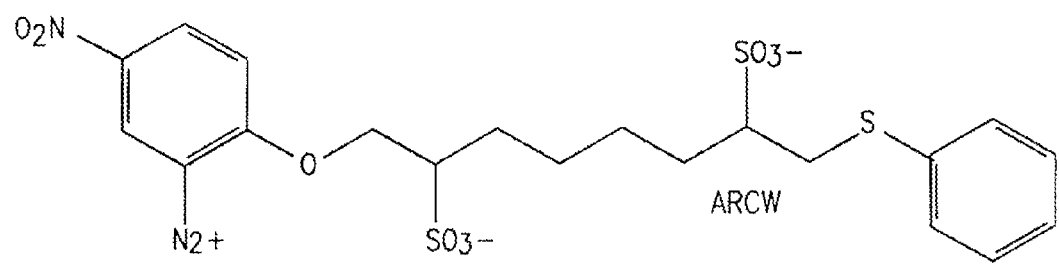
FIG. 4B is a diagrammatic representation of the chemical structure of the Analyte Reactive Coating soluble in Water (ARCW).
Figure 4C:
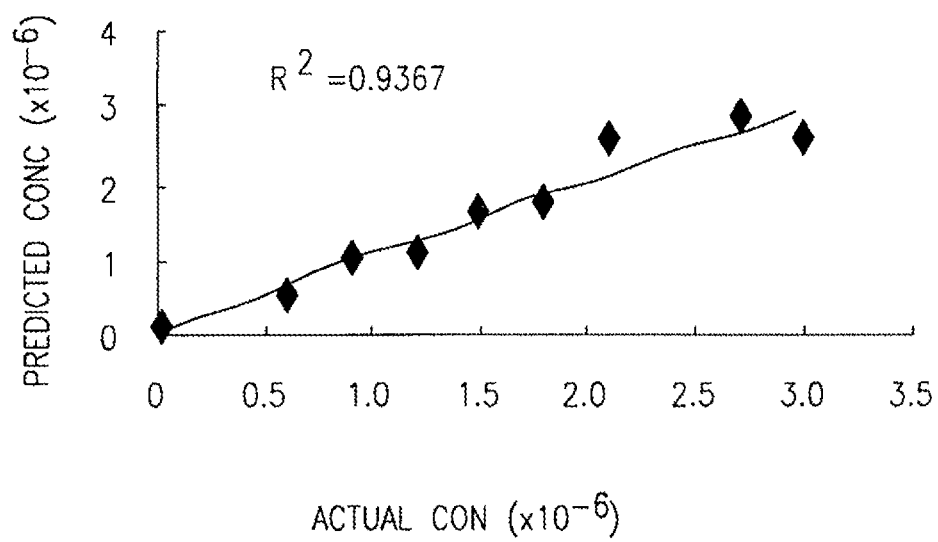
FIG. 4C is a correlation plot between actual concentration and predicted concentration for a reconstituted lyophilized colloid solution with 0.05% w/w PEG and RB 15 dye and a reagent of ARCW.

FIG. 4B shows a reagent of Analyte Reactive Coating soluble in Water (ARCW). Using this reagent in blood collecting tubes, a PLS model was made with bilirubin. FIG. 4A represents a spectrum of this PLS correlation model. The blood collecting tubes were prepared using the same procedure described above. In addition to lyophilizing the colloid in the tubes, 1 µL of 0.00299 M Diazonium ARCW was added to the opposite end from the colloid of each tube and also lyophilized. The tubes were then placed in a vacuum to remove the water from the colloid suspension and ARCW solution. A $2.99 \times 10^{-4}$ M stock solution of bilirubin was prepared by dissolving 0.00175 g of bilirubin in a 5:4:1 ethanol, water, saturated bicarbonate solution. A $2.99 \times 10^{-6}$ M solution of bilirubin was prepared by diluting with Millipore $H_2O$, 100 µL of the stock solution to 9.8 mL $H_2O$+ 100 µL 0.05 M KOH. A concentration range $5.98 \times 10^{-7}$ to $2.99 \times 10^{-6}$ M bilirubin was prepared. In the lyophilized tubes 100 µL of each concentration and a Teflon coated iron rod was added to the end of the tube, which contained the ARCW. This was allowed to set for 5 min, after which the solution was mixed with the colloid and a spectrum was taken. FIG. 4C shows the result for 0.05M KOH 100 µL in 9.8 mL $H_2O$ and 100 µL bilirubin, in a correlation plot between actual concentration and predicted concentration with a $R^2=0.9367$.

Figure 5:
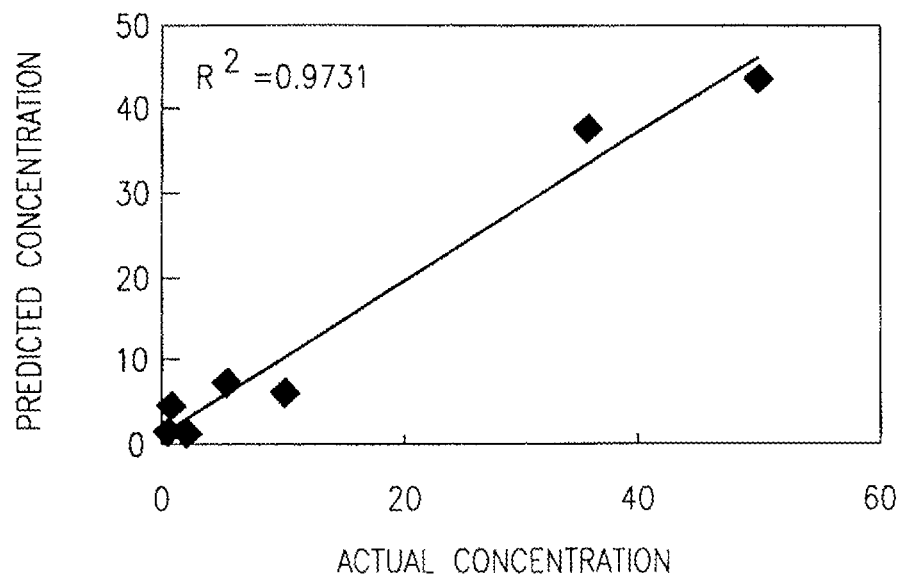
FIGS. 5 and 6 are PLS cross-validation plots of actual versus predicted hGH concentration levels for a Surface Enhanced Raman ImmunoAssay (SERIA) analysis using a lyophilized silver colloidal base according to the present invention.

FIG. 5 shows a PLS cross-validation plot of actual versus predicted human Growth Hormone (hGH) concentration levels for a Surface Enhanced Raman ImmunoAssay (SERIA) analysis using a lyophilized silver colloidal base. A Lee and Meisel silver colloidal suspension (R) was prepared to which was added a 1:400,000 dilution of polyclonal hGH antibody (Ab). This addition is accomplished by slowly adding small aliquots of the antibody solution (140 µL total) to 1 mL of the colloidal suspension with gentle agitation with continued mixing for 15 min. A stabilizer of polyethylene glycol (PEG, ave. 15000 MW) was added to the solution to make a 5% solution of PEG/RhGHAb. A mini-microwell plate (NUNC®) was used as the sample container for the analysis. To each of 10 wells of the plate was added 20 µL of the PEG/RhGHAb solution. The plate was placed in liquid nitrogen to 'flash' freeze the wells of solution and then placed in a high vacuum vial set in a cooling container of dry ice. The vacuum vial was then attached to the lyophilizer for 24 hr. Each well of lyophilized colloidal base appeared as a light tan colored waxy semi-solid. The addition of liquid immediately reconstituted the base to produce a light tan colored colloidal suspension resembling the original solution. The analysis was completed by the addition of varying concentration of hGH antigen in an aqueous sodium bicarbonate solution (1%), followed by the addition of a reporter molecule solution. The solution of antigen was used to reconstitute the lyophilized PEG/RhGHAb for the assay.

Figure 6:
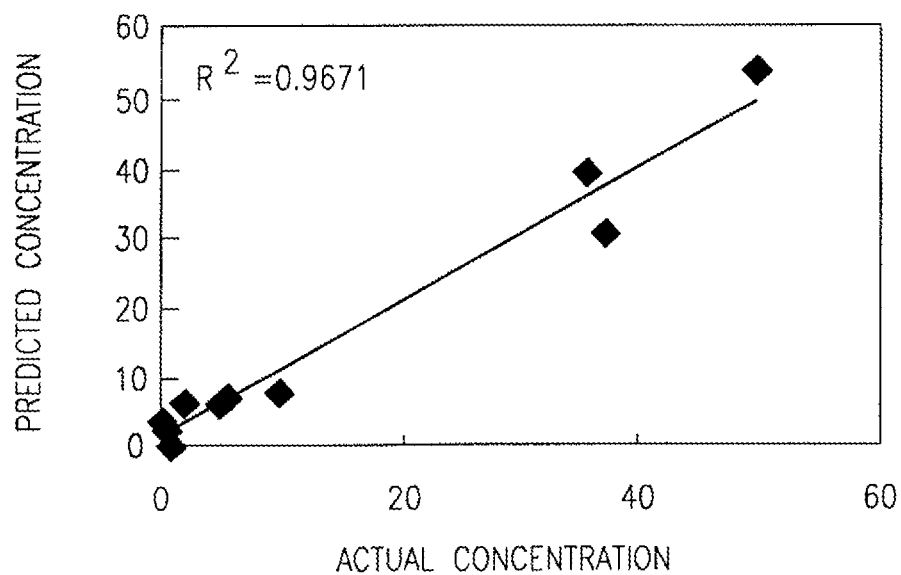

FIG. 6 shows a PLS cross-validation plot of actual versus predicted hGH concentration levels for a SERIA analysis similar to that described above. In this instance, the lyophilized colloidal base was a 0.5% PEG/RhGHAb. After lyophilization, the wells of colloidal base appeared as tan colored nugget with a puckered surface. Addition of the antigen solution caused complete reconstitution of the colloidal base.

While the foregoing invention has been described with reference to the above embodiments, various modifications and changes can be made without departing from the spirit of the invention. Accordingly, all such modifications and changes are considered to be within the scope of the appended claims.

What is claimed is:

1. A method of analyzing a material, the method comprising the steps of:
    mixing a colloid with a pretreatment material, the colloid consisting of a suspension of colloidal particles of a metal, wherein the pretreatment prevents the colloidal particles of the suspension from sticking to one another;
    placing a known mass of the suspension of colloidal particles of the metal mixed with the pretreatment material in a first section of a container;
    placing a water soluble analyte reactive coating comprising a reagent that is reactive to the analyte in a second section of the container;
    lyophilizing the reagent and the colloidal particles of the metal mixed with the pretreatment material to produce an assay;
    simultaneously reconstituting and mixing the assay with the material to be analyzed to produce a Surface Enhanced Raman Scattering active solution, the colloidal particles of metal of the Surface Enhanced Raman Scattering active solution defining a Surface Enhanced Raman Scattering active metal surface and the reagent coupling the material to the Surface Enhanced Raman Scattering active metal surface;
    performing Surface Enhanced Raman Scattering spectroscopy on the Surface Enhanced Raman Scattering active solution to analyze the material.

2. The method of claim 1, wherein the metal is a noble metal.

3. The method of claim 1, wherein the pretreatment material comprises a wax-like material.

4. The method of claim 1, wherein the pretreatment material comprises polyethylene glycol.

5. The method of claim 1, wherein the second section of the container is remote from the first section of the container.

6. The method of claim 1, wherein the container includes a pretreatment applied to an inner surface of the container, the pretreatment for preventing the particles from sticking to the inner surface of the container.

7. The method of claim 6, wherein the pretreatment comprises a wax-like material.

8. The method of claim 6, wherein the pretreatment comprises polyethylene glycol.

9. The method of claim 1, wherein the container includes a plurality of chambers, each of the chambers having a first section.

10. The method of claim 9, wherein the placing step includes placing the suspension of colloidal particles of the metal mixed with the material to be analyzed in the first section of each of the chambers of the container.

11. The method of claim 1, wherein the container includes a plurality of chambers, each of the chambers having a first section and a second section.

12. The method of claim 11, wherein the step of placing the known mass of the suspension of colloidal particles of the metal includes placing a known mass of the suspension of colloidal particles of the metal mixed with the material in the first section of each of the chambers of the container.

13. The method of claim 11, wherein the step of placing the reagent includes placing the reagent of the analyte reactive coating soluble in water in the second section of each of the chambers of the container.

14. The method of claim 1, wherein the reagent comprises Diazonium.

* * * * *